(12) United States Patent
Sun et al.

(10) Patent No.: US 12,097,381 B2
(45) Date of Patent: Sep. 24, 2024

(54) INTEGRATED TMS COIL FOR BRAIN TESTING AND TREATMENT

(71) Applicant: WUHAN ZNION TECHNOLOGY CO., LTD, Hubei (CN)

(72) Inventors: Cong Sun, Hubei (CN); Bo Wang, Hubei (CN); Shengan Cai, Hubei (CN)

(73) Assignee: WUHAN ZNION TECHNOLOGY CO., LTD (CN)

( * ) Notice: Subject to any disclaimer, the term of this patent is extended or adjusted under 35 U.S.C. 154(b) by 402 days.

(21) Appl. No.: 17/284,156

(22) PCT Filed: May 9, 2019

(86) PCT No.: PCT/CN2019/086108
§ 371 (c)(1),
(2) Date: Apr. 9, 2021

(87) PCT Pub. No.: WO2020/223942
PCT Pub. Date: Nov. 12, 2020

(65) Prior Publication Data
US 2021/0330987 A1    Oct. 28, 2021

(51) Int. Cl.
| A61N 2/00 | (2006.01) |
| A61B 5/00 | (2006.01) |
| A61N 2/02 | (2006.01) |
| G02B 6/36 | (2006.01) |
| H05K 7/20 | (2006.01) |

(52) U.S. Cl.
CPC ............ *A61N 2/006* (2013.01); *A61B 5/0042* (2013.01); *A61B 5/0075* (2013.01); *A61N 2/02* (2013.01); *G02B 6/3616* (2013.01); *H05K 7/20272* (2013.01)

(58) Field of Classification Search
None
See application file for complete search history.

(56) References Cited

U.S. PATENT DOCUMENTS

| 6,542,763 | B1 * | 4/2003 | Yamashita | ........... A61B 5/0042 |
| | | | | 600/344 |
| 2007/0083097 | A1 * | 4/2007 | Fujiwara | .............. A61B 5/0042 |
| | | | | 600/407 |

(Continued)

FOREIGN PATENT DOCUMENTS

CN        103007432        *    4/2013

OTHER PUBLICATIONS

English translation of Lu (CN 103007432) (Year: 2013).*

*Primary Examiner* — Katherine L Fernandez

(57) ABSTRACT

An integrated Transcranial Magnetic Stimulation (TMS) coil for brain function testing and treatment is provided. The coil includes a coil housing. A figure-eight coil is provided inside the coil housing, and the coil housing is provided with two waist-like bosses for limiting a position of the coil, eight mounting holes are formed on the coil housing, and an optical fiber holder is provided in each of the mounting holes for mounting an optical fiber probe, a silica gel sheet is provided inside the coil housing for limiting movement of the optical fiber holders, a lead-out of the coil passes through the bottom of the coil housing and is connected to a TMS instrument, and a signal end of the optical fiber probe is connected to a near-infrared brain function imager.

8 Claims, 5 Drawing Sheets

(56) References Cited

U.S. PATENT DOCUMENTS

| | | | |
|---|---|---|---|
| 2008/0058581 A1* | 3/2008 | Aho | A61N 2/02 |
| | | | 600/13 |
| 2008/0262327 A1* | 10/2008 | Kato | A61B 5/0042 |
| | | | 600/324 |
| 2014/0249352 A1* | 9/2014 | Zangen | A61N 2/006 |
| | | | 600/13 |
| 2014/0343351 A1* | 11/2014 | Tojo | A61B 90/50 |
| | | | 600/14 |

* cited by examiner

INTEGRATED TMS COIL FOR BRAIN TESTING AND TREATMENT

FIELD

The present invention relates to the technical field of brain function testing and Transcranial Magnetic Stimulation (TMS) diagnosis and treatment devices, and in particular, to an integrated TMS coil for brain function testing and treatment.

BACKGROUND

TMS diagnosis and treatment technology is a new technology for non-invasive cerebral cortex stimulation and modulation that appeared after 1985. It has been widely used in brain science research and clinical diagnosis and treatment. TMS uses a pulsed transient magnetic field to pass through the skull without hindrance and pain, and induces currents in the skull to stimulate the cerebral cortical nerves to produce a series of physiological and biochemical reactions. TMS affects all levels of molecules, synapses, cells, networks, functional areas, system structures, and decision-making behavior in neuroscience. In recent years, it has received increasing attention in the fields of physical medicine and rehabilitation, psychiatry, neuroscience, etc., and has been gradually promoted in clinical and scientific research.

The principle of TMS modulating nerve function is to use different stimulation modes and stimulation parameters to act on local nerves and networks, bidirectionally regulating the strength of synaptic connections of nerves, that is, modulating the long-term enhancement or long-term inhibition of the nerve function, and bidirectionally regulating the nerve excitability, regulating the local cerebral blood flow and metabolism, and using this to regulate the nerve function and treat neurological dysfunction diseases.

TMS is often used to stimulate the motor area of the cerebral cortex, which can make the target muscle controlled by the motor nerve contract and shake. The amplitude of the motor evoked potential on the target muscle is often used to test the stimulation effect, determine the stimulation parameters, and artificially interfere with the nerve function according to a predetermined target to modulate the excitability of the motor nerve. Now it has been discovered that stimulating the rest of the brain (such as the dorsolateral frontal lobe, temporal lobe, and parietal lobe) can treat some neuropsychiatric dysfunction diseases such as depression and schizophrenia, but the stimulation effect can be detected by stimulating these parts without target organs. The effect of conventional high-frequency stimulation is affected by a large variety of factors. These uncertain factors require the correct selections of the stimulation modes and parameters. If the stimulation effect cannot be detected in real time, it is impossible to determine the change in the oxygen consumption of the stimulation site, and thus, it is difficult to determine the effect of TMS on the stimulation site and determine the therapeutic effect of TMS, which hinders the application, development, and promotion of TMS.

The excitement and activity of the brain increase metabolism and oxygen consumption. Therefore, at present, only functional magnetic resonance and positron emission tomography imaging systems are used to detect the changes in cerebral blood flow and biochemical metabolism of the non-motor area of the brain stimulated by TMS to determine the therapeutic effect after TMS stimulation. However, the two devices are very expensive, the testing time is long, the head cannot move during the testing process, the therapeutic effect cannot be detected in real time during the treatment process, and the parameters of TMS magnetic stimulation treatment cannot be adjusted according to the real-time therapeutic effect, which reduces the therapeutic effect.

Chinese patent having the application No. CN103007432B discloses an integrated device for brain function modulation and testing on Jul. 1, 2015. A silica gel sleeve is sleeved on the surface of a TMS coil. Several holes at different distances are provided on an inner ring and an outer ring of the silica gel sleeve for facilitating inserting near-infrared transmitting and receiving probes. Due to the elasticity of the silica gel sleeve, the probes can be firmly held and upper and lower positions of the probes can be freely adjusted to ensure that the probes are in close contact with the scalp of the detection site. A miniature near-infrared brain function testing device uses a processor to respectively set the transmitting and receiving frequencies of near-infrared rays having wavelengths of 690 nm and 830 nm. A time division multiplexing mode is used to sequentially light up several LD/LED transmitting light sources in turn distributed at the central part of a stimulation coil. Signals detected by surrounding probes are processed and display the changes in deoxygenated hemoglobin and blood flow on a liquid crystal screen to reflect the changes in the strength, range, and depth of functional activities of the brain regions corresponding to sites of each detection channel during TMS. The coil in the prior art still has a large variety of problems that need to be solved urgently, such as the arrangement scheme of the probe of how to arrange the probes to perfectly integrate a detection region of the probe with a treatment region of the TMS coil to achieve an optimal therapeutic effect and testing effect while ensuring that the optical fiber probe and the structure of the TMS coil do not interfere with each other; how to improve the comfort of patients during treatment and testing; in addition, for the large heat generated during the TMS coil operation, how to arrange a heat-dissipation system to ensure a good heat-dissipation effect without affecting the internal structure of the TMS coil.

SUMMARY

The purpose of the present invention is to provide an integrated TMS coil for brain function testing and treatment for the existing problems in the prior art. Optical fiber probes are mounted on the TMS coil, a therapeutic effect is detected in real time by a near-infrared brain function imager, and stimulation parameters of the TMS coil are adjusted according to the therapeutic effect, so as to achieve an optimal therapeutic effect.

In order to achieve the purpose above, the technical solution of the present invention is:

an integrated TMS coil for brain function testing and treatment, including a coil housing, where a figure-eight coil is provided inside the coil housing, the coil housing is provided with two waist-like bosses, and the two waist-like bosses are embedded in two inner rings of the coil for limiting a position of the coil; the two waist-like bosses are each formed with two mounting holes, and two mounting holes are formed at each of the upper and lower sides of an outer ring of the coil; the mounting holes are each provided with an optical fiber holder for mounting an optical fiber probe; a silica gel sheet is provided inside the coil housing, eight through holes are formed on the silica gel sheet, positions of the eight through holes respectively correspond to those of the eight mounting holes on the coil housing, and the through holes on the silica gel sheet are sleeved inside the optical fiber holders for limiting movement of the optical fiber holders; a lead-out of the coil passes through the bottom of the coil housing and is connected to a TMS instrument; a signal end of the optical fiber probe is connected to a near-infrared brain function imager, a probing end of the optical fiber probe passes through the back and the front of the coil housing, and movement of the optical fiber probe is limited by the optical fiber holder and the silica gel sheet provided inside the coil housing.

Specifically, the positions of the eight mounting holes on the coil housing are defined as: a plane rectangular coordinate system is created by using the central point of the coil as an origin, the horizontal direction as X axis, and the vertical direction as Y axis; the coordinates of the mounting holes on the two waist-like bosses from left to right are respectively: (−45, 0), (−15, 0), (15, 0), and (45, 0); the coordinates of the two mounting holes at the upper side of the outer ring of the coil from left to right are respectively: (−15, 30) and (15, 30); the coordinates of the two mounting holes at the lower side of the outer ring of the coil from left to right are respectively: (−15, −30) and (15, −30); the two mounting holes on the waist-like boss are arranged close to the edges of the inner rings of the coil, and the four mounting holes at the upper and lower sides of the outer ring of the coil housing are arranged close to the edges of the outer rings of the coil. By using this arrangement approach, a therapeutic region of the coil can overlap with a detection region of the optical fiber probe to the greatest extent so as to ensure the testing and therapeutic effects while making full use of the space inside the TMS coil, and the testing and treatment run independently and synchronously, and do not interfere with each other.

Specifically, the optical fiber probes include four transmitting optical fiber probes and four receiving optical fiber probes; the eight mounting holes are respectively used for mounting the four transmitting optical fiber probes and the four receiving optical fiber probes; the two mounting holes on the waist-like boss are respectively used for mounting one transmitting optical fiber probe and one receiving optical fiber probe; and the two mounting holes at the upper side/lower left of the outer ring of the coil are respectively used for mounting one transmitting optical fiber probe and one receiving optical fiber probe.

Specifically, the coil is formed by winding a hollow copper tube, and the interior of the hollow copper tube is used for circulating a cooling liquid; a water inlet and a water outlet are formed at a position where the coil is connected to the TMS instrument, and the water inlet and the water outlet are respectively in communication with two ports of the hollow copper tube; a TMS host, a water pump, a water tank, and a radiator are provided inside the TMS instrument; the water pump is separately in communication with the water tank and the water inlet, and the radiator is separately in communication with the water outlet and the water tank; and the cooling liquid is circulated in the water tank, the hollow copper tube, and the radiator to cool the coil. By introducing the cooling liquid into the hollow copper tube, the hollow copper tube serves as a TMS coil and a cooling water tube simultaneously, which saves the space inside the TMS coil and improves the heat-dissipation effect.

Specifically, the optical fiber holder includes an annular boss and a nut, and the nut is threadedly connected to the annular boss; the inner diameter of the annular boss is slightly less than the outer diameter of the optical fiber probe to facilitate sleeving of an optical fiber; the outer diameter of the upper part of the annular boss is greater than the caliber of the through hole on the silica gel sheet, and the through hole on the silica gel sheet is sleeved on the upper part of the annular boss. The optical fiber holder can perform linear reciprocating motion within the elastic limit of the silica gel sheet along the hole passing direction of the mounting hole. The silica gel sheet plays a role of fixing the optical fiber holder, and allows the optical fiber holder to have a certain movement space, which makes it convenient for the optical fiber probe to be attached to the scalp of a patient more tightly and prevents the optical fiber probe from falling and affecting the testing result without causing damage to the scalp of the patient caused by the excessive compression.

Specifically, a buffer silica gel head is provided on the end of the optical fiber probe in contact with the scalp of the patient, and is used for buffering the damage of the optical fiber probe on the scalp of the patient, which improves the comfort of the patient.

Specifically, the optical fiber holder is made of non-metal, which has the purpose of preventing the interference of a magnetic field generated by the TMS coil to affect the therapeutic effect.

Specifically, several cable tie holes are formed on the side surface of the coil housing, which has the function of enabling a cable tie or a ribbon to pass through the cable tie hole to fix the TMS coil and the head of the patient and preventing the TMS coil from not tightly attaching to the head of the patient.

Specifically, the front of the coil housing is a concave arc surface, and the radius of the concave arc surface is 100 mm; and the front of the coil housing is configured as a concave arc surface to better attach the TMS coil to the head of the human body.

Specifically, the coil housing is made of an insulating and thermal insulating material.

Compared with the prior art, the beneficial effects of the present invention are: (1) in the present invention, mounting holes are formed on the coil housing for mounting the optical fiber probes; the signal end of the optical fiber probe is connected to the near-infrared brain function imager so as to detect the therapeutic effect by the near-infrared brain function imager in real time in the process of performing magnetic stimulation treatment using the TMS coil, and then adjust parameters of the TMS coil according to the therapeutic effect, which greatly improves the therapeutic effect of the TMS coil; (2) in the present invention, the optical fiber probes arranged on the coil housing and the TMS coil do not interfere with each other, and independently and simultaneously work, which makes full use of the internal space of the coil, and greatly decreases the volume of the TMS coil; moreover, all the optical fiber probes are arranged close to the edges of the inner rings/outer rings of the TMS coil, so that the detection region of the optical fiber probe overlaps with the treatment region of the TMS coil to the greatest extent, and the testing and treatment are fed back in real time, and verify mutually, which improves the accuracy of testing and the effectiveness of treatment; (3) in the present invention, the optical fiber probes are embedded inside the through holes on the silica gel sheet through the optical fiber holders, so that the optical fiber probes can perform linear reciprocating motion only within the elastic limit range of the silica gel sheet along the hole passing direction of the mounting holes on the coil housing, which makes it convenient for the optical fiber probe to be attached to the scalp of the patient more tightly and prevents the optical fiber probe from falling and affecting the testing result without causing damage to the scalp of the patient caused by the excessive compression; (4) in the present invention, the cooling liquid is introduced into the coil (the hollow copper tube) for cooling the TMS coil; the hollow copper tube serves as a TMS coil and a cooling water tube simultaneously, which saves the space inside the TMS coil and improves the heat-dissipation effect.

Figure 1:
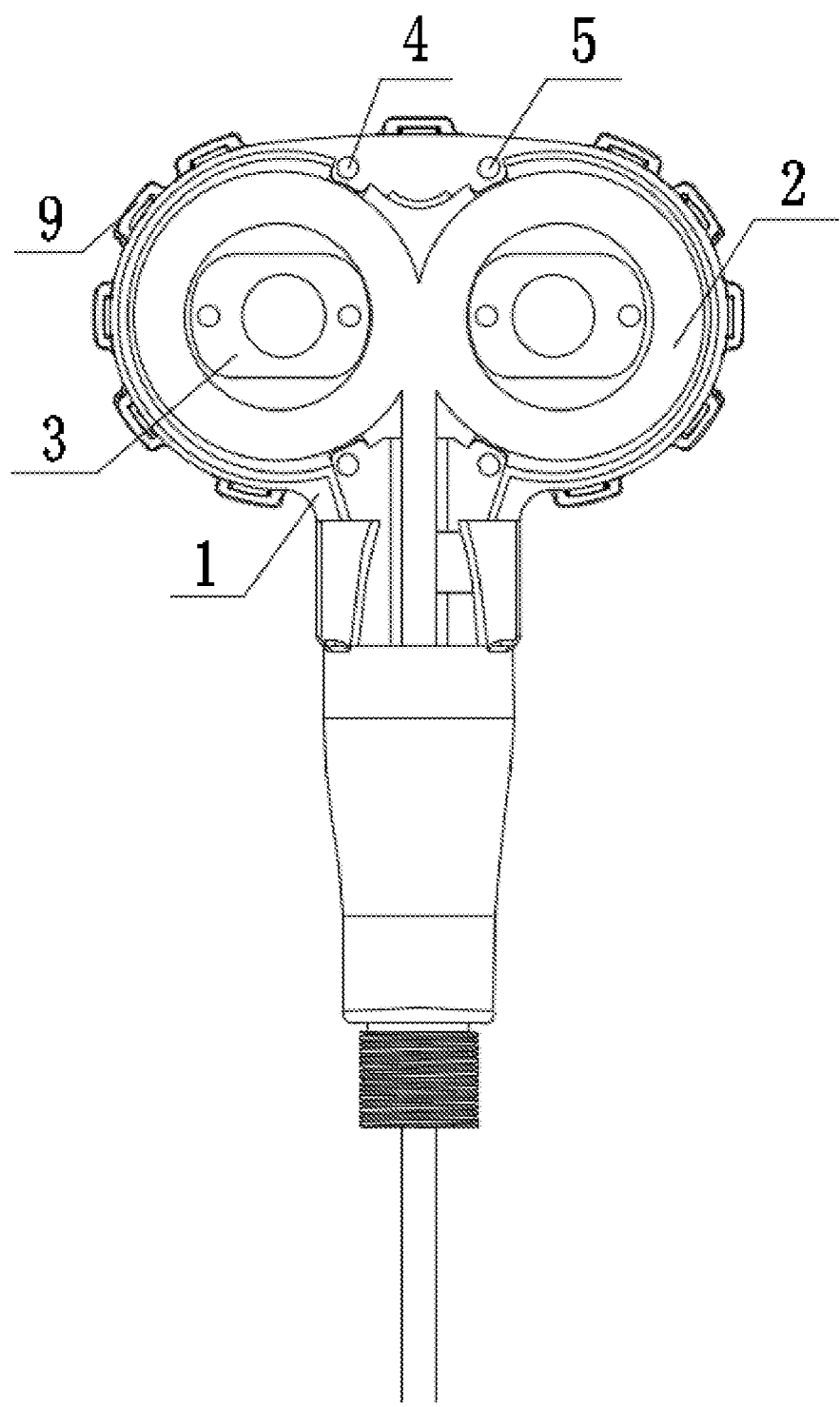
FIG. 1 is a schematic structural diagram of an entire integrated TMS coil for brain function testing and treatment of the present invention.

Reference numerals: 1. coil housing; 2. coil; 3. waist-like boss; 4. first mounting hole; 5. second mounting hole; 6. optical fiber probe; 7. optical fiber holder; 8. buffer silica gel head; 9. cable tie hole; 10. annular boss; 11. nut; 12. silica gel sheet; 13. through hole; 14. TMS instrument; 15. near-infrared brain function imager.

DETAILED DESCRIPTION

The technical solutions of the present invention are clearly and fully described below with reference to the accompanying drawings in the present invention. Apparently, the described embodiments are merely some of the embodiments of the present invention, but not all the embodiments. Based on the embodiments of the present invention, all other embodiments obtained by persons of ordinary skill in the art without involving an inventive effort shall fall within the scope of protection of the present invention.

Embodiment 1

Figure 4:
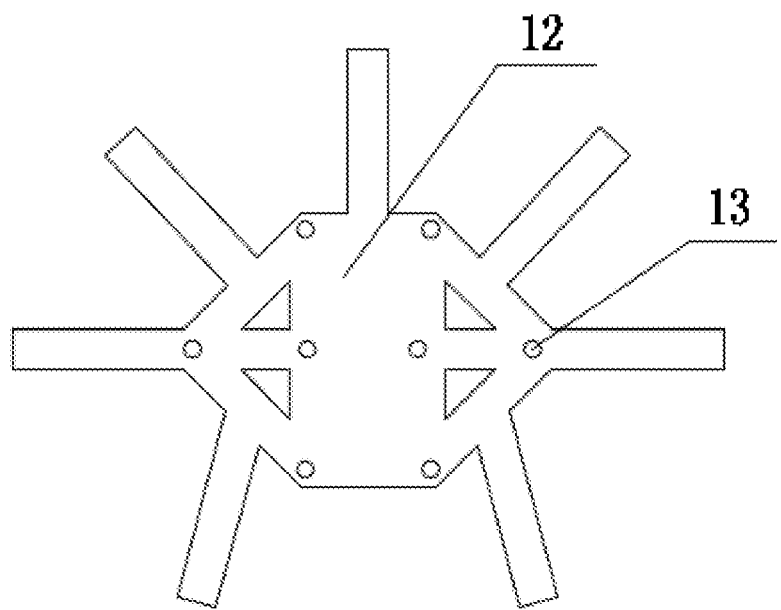
FIG. 4 is a schematic distribution diagram of through holes on a silica gel sheet of the present invention.
Figure 5:
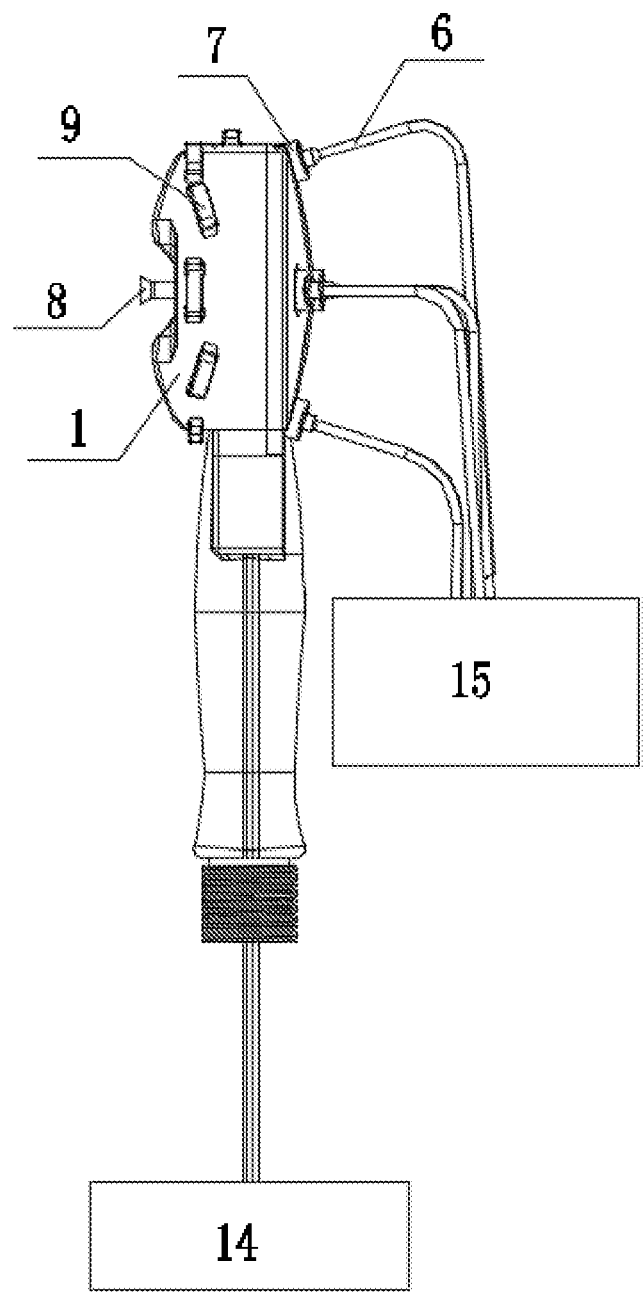
FIG. 5 is a schematic diagram where a TMS coil is connected to a TMS instrument and a near-infrared brain function imager in embodiments of the present invention.

As shown in FIGS. 1, 4, and 5, this embodiment provides an integrated TMS coil for brain function testing and treatment, including a coil housing 1. A figure-eight coil 2 is provided inside the coil housing 1. The coil housing 1 is provided with two waist-like bosses 3. The two waist-like bosses 3 are embedded in two inner rings of the coil 2 for limiting a position of the coil, and are respectively provided with two mounting holes. Two mounting holes are respectively at upper and lower sides of an outer ring of the coil 2. The mounting holes are each provided with optical fiber holders 7 for mounting optical fiber probes 6. A silica gel sheet 12 is provided inside the coil housing 1, and is provided with eight through holes 13. Positions of the eight through holes 13 respectively correspond to those of eight mounting holes on the coil housing 1. The through holes 13 on the silica gel sheet 12 are sleeved inside the optical fiber holders 7 for limiting movement of the optical fiber holders. a lead-out of the coil 2 passes through the bottom of the coil housing 1 and is connected to a TMS instrument 14. A signal end of the optical fiber probe 6 is connected to a near-infrared brain function imager 15. A probing end of the optical fiber probe 6 passes through the back and the front of the coil housing 1. The movement of the optical fiber probe 6 is limited by the optical fiber holder 7 and the silica gel sheet 12 provided inside the coil housing 1. Both the testing principle of the near-infrared brain function imager 15 and the working principle of a TMS diagnosis and treatment device are prior arts, and will not be illustrated here.

Figure 3:
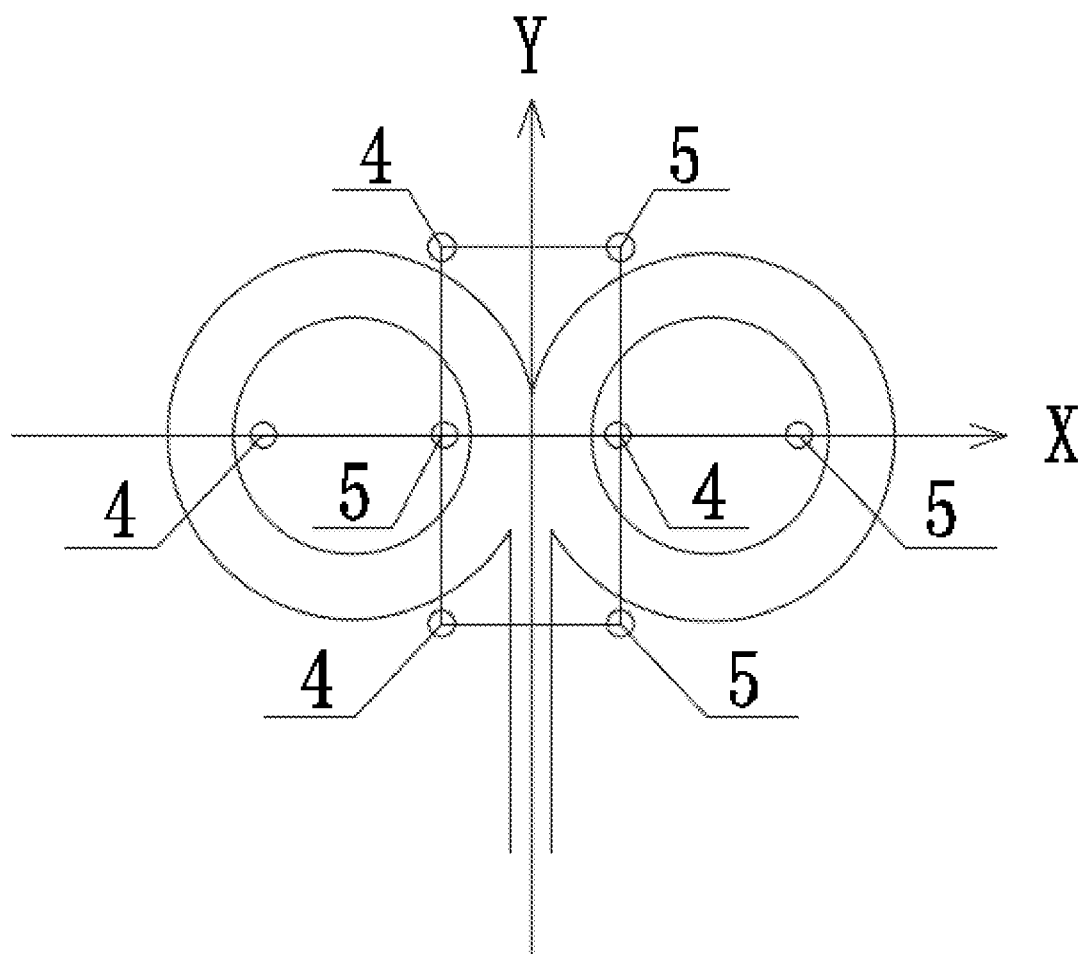
FIG. 3 is a schematic structural diagram of arrangements of mounting holes and a coil on a coil housing of the present invention.

Specifically, as shown in FIG. 3, the positions of the eight mounting holes on the coil housing 1 are defined as: a plane rectangular coordinate system is created by using the central point of the coil 2 as an origin, the horizontal direction as X axis, and the vertical direction as Y axis. The coordinates of the mounting holes on the two waist-like bosses 3 from left to right are respectively: (−45, 0), (−15, 0), (15, 0), and (45, 0). The coordinates of the two mounting holes at the upper side of the outer ring of the coil 2 from left to right are respectively: (−15, 30) and (15, 30). The coordinates of the two mounting holes at the lower side of the outer ring of the coil 2 from left to right are respectively: (−15, −30) and (15, −30). The two mounting holes on the waist-like boss 3 are arranged close to the edges of the inner rings of the coil 2. The four mounting holes at the upper and lower sides of the outer ring of the coil housing 1 are arranged close to the edges of the outer rings of the coil 2. The coordinates of edge extreme points of the coil 2 in left, right, up, and down directions are respectively: (−65, 0), (65, 0), (−30, 32.5)/(30, 32.5) and (−30, −32.5)/(30, −32.5). By using this arrangement approach, a treatment region of the coil 2 can overlap with a detection region of the optical fiber probe 6 to the greatest extent so as to ensure the testing and therapeutic effects while making full use of the space inside the TMS coil, and the testing and treatment run independently and synchronously, and do not interfere with each other.

Specifically, the optical fiber probe 6 includes four transmitting optical fiber probes and four receiving optical fiber probes. The eight mounting holes include four first mounting holes 4 and four second mounting holes 5. The first mounting holes 4 are used for mounting the transmitting optical fiber probes. The second mounting holes 5 are used for mounting the receiving optical fiber probes. The mounting hole on the left of the waist-like boss 3 is the first mounting hole 4, which is used for mounting the transmitting optical fiber probe. The mounting hole on the right of the waist-like boss 3 is the second mounting hole 5, which is used for mounting the receiving optical fiber probe. The mounting holes on the left of the upper side/lower side of the outer ring of the coil 2 are first mounting holes 4, which are used for mounting the transmitting optical fiber probes. The mounting holes on the right of the upper side/lower side of the outer ring of the coil 2 are second mounting holes 5, which are used for mounting the receiving optical fiber probes.

Figure 2:
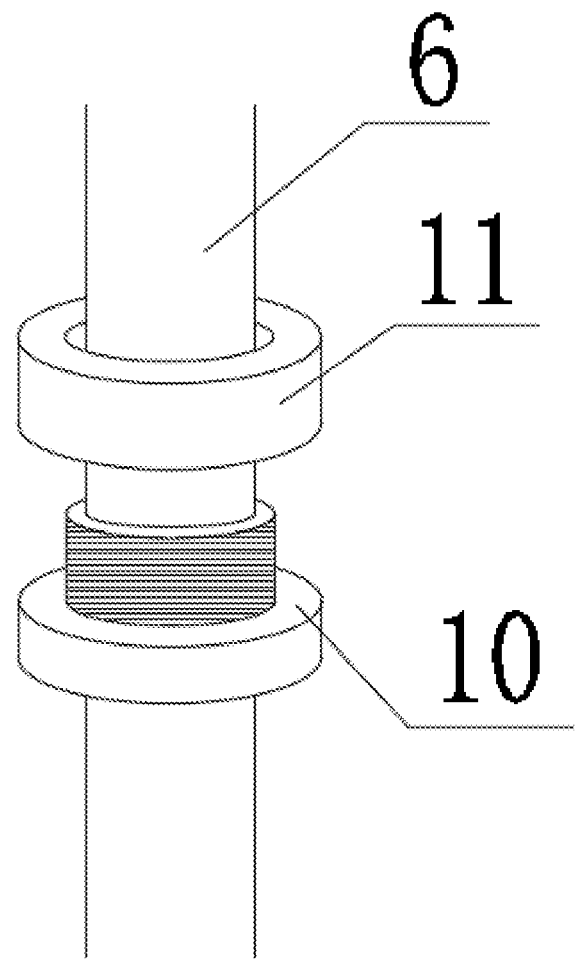
FIG. 2 is a schematic structural diagram of optical fiber holders of the present invention.

Specifically, as shown in FIG. 2, the optical fiber holder 7 includes an annular boss 10 and a nut 11. The nut 11 is threadedly connected to the annular boss 10. The inner diameter of the annular boss 10 is slightly less than the outer diameter of the optical fiber probe 6 to facilitate sleeving of an optical fiber. The outer diameter of the upper part of the annular boss 10 is greater than the caliber of the through hole 13 on the silica gel sheet 12. The through hole 13 on the silica gel sheet 12 is sleeved on the upper part of the annular boss 10. The optical fiber holder 7 can perform linear reciprocating motion within the elastic limit of the silica gel sheet 12 along the hole passing direction of the mounting hole. The silica gel sheet 12 plays a role of fixing the optical fiber holder 7, and allows the optical fiber holder 7 to have a certain movement space, which makes it convenient for the optical fiber probe 6 to be attached to the scalp of a patient more tightly and prevents the optical fiber probe 6 from falling and affecting the testing result without causing damage to the scalp of the patient caused by the excessive compression.

Further, when the TMS coil in this embodiment is assembled, first, the eight through holes 13 on the silica gel sheet 12 are respectively sleeved on the annular boss 10 of eight optical fiber holders 7, and then the nut 11 is tightened; next, the coil 2 is placed inside the coil housing 1, and the two inner rings of the coil 2 are fastened by the two waist-like bosses 3; the silica gel sheet 12 is placed onto the coil 2 to enable the eight through holes 13 on the silica gel sheet 12 to align with the eight mounting holes on the housing; the eight optical fiber probes 6 separately pass through a rear cover of the coil housing 1, are inserted into the optical fiber holders 7, and extracted from the front of the coil housing 1 about 3 cm; and then the rear cover of the coil housing 1 is covered.

Specifically, a buffer silica gel head 8 is provided on the end of the optical fiber probe 6 in contact with the scalp of the patient, and is used for buffering the damage of the silica gel probe on the scalp of the patient, which improves the comfort of the patient. The buffer silica gel head 8 is dark, which has the function of protecting from light, and prevents the interference of the external light so as to further improve the testing accuracy.

Specifically, the optical fiber holder 7 is made of non-metal, which has the purpose of preventing the interference of a magnetic field generated by the TMS coil 2 to affect the therapeutic effect.

Specifically, several cable tie holes 9 are provided on the side surface of the coil housing 1, which has the function of enabling a cable tie or a ribbon to pass through the cable tie hole 9 to fix the TMS coil and the head of the patient and preventing the TMS coil from not tightly attaching to the head of the patient.

Specifically, the front of the coil housing 1 is a concave arc surface, and the radius of the concave arc surface is 100±10 mm. The front of the coil housing 1 is configured as a concave arc surface to better attach the TMS coil to the head of the human body.

Embodiment 2

This embodiment provides an integrated TMS coil for brain function testing and treatment, and differs from embodiment 1 in that in this embodiment, the coil 2 is formed by winding a hollow copper tube. The interior of the hollow copper tube is used for circulating a cooling liquid. A water inlet and a water outlet are formed at a position where the coil 2 is connected to a TMS instrument 14. The water inlet and the water outlet are respectively in communication with two ports of the hollow copper tube. A TMS host, a water pump, a water tank, and a radiator are provided inside the TMS instrument 14. The water pump is separately in communication with the water tank and the water inlet. The radiator is separately in communication with the water outlet and the water tank. The cooling liquid is circulated in the water tank, the hollow copper tube, and the radiator to cool the coil 2. By introducing the cooling liquid into the hollow copper tube, the hollow copper tube serves as a TMS coil and a cooling water tube simultaneously, which saves the space inside the TMS coil and improves the heat-dissipation effect.

When the TMS coil needs to be disassembled from the TMS instrument 14, liquid drainage treatment needs to be performed first through the water pump, and the TMS coil can be removed after the cooling liquid inside the TMS coil is completed draining. The water pump, the radiator, and the TMS host in this embodiment run synchronously. When the TMS coil is powered on, the cooling liquid starts to be introduced for cooling the coil 2, which can effectively decrease the temperature during the TMS coil operation.

Further, the radiator includes a heat-dissipation tube and a heat-dissipation fan. The heat-dissipation fan is used for dissipating the heat inside the heat-dissipation tube into the external air.

Although the embodiments of the present invention are illustrated and described, it can be understood that persons of ordinary skill in the art can make various changes, modifications, substitutions and variations on these embodiments without departing the principle and spirit of the present invention. The scopes of the present invention are defined by the appended claims and equivalents thereof.

What is claimed is:

1. An integrated Transcranial Magnetic Stimulation (TMS) coil for brain function testing and treatment, comprising a coil housing, wherein,
   a figure-eight coil is provided inside the coil housing, the coil housing is provided with two bosses, and the two bosses are embedded in two inner rings of the coil for limiting a position of the coil;
   the two bosses are each formed with two mounting holes, and two additional mounting holes are formed at each of an upper and lower sides of an outer ring of the coil;
   the mounting holes are each provided with an optical fiber holder for mounting an optical fiber probe;
   a silica gel sheet is provided inside the coil housing, eight through holes are formed on the silica gel sheet, positions of the eight through holes respectively correspond to those of the eight mounting holes on the coil housing, and the through holes on the silica gel sheet are sleeved inside the optical fiber holders for limiting movement of the optical fiber holders;
   a lead-out of the coil passes through a bottom of the coil housing and is connected to a TMS instrument; and
   a signal end of each optical fiber probe is connected to a near-infrared brain function imager, a probing end of each optical fiber probe passes through a back and a front of the coil housing, and movement of each optical fiber probe is limited by the respective optical fiber holder and the silica gel sheet provided inside the coil housing;
   wherein, the positions of the eight mounting holes are defined as: a plane rectangular coordinate system created by using a central point of the coil as an origin, a horizontal direction as X axis, and a vertical direction as Y axis;
   coordinates of the mounting holes on the two bosses from left to right are respectively: (−45, 0), (−15, 0), (15, 0), and (45, 0); coordinates of the two mounting holes at the upper side of the outer ring of the coil from left to right are respectively: (−15, 30) and (15, 30); and coordinates of the two mounting holes at the lower side of the outer ring of the coil from left to right are respectively: (−15, −30) and (15, −30);
   the optical fiber probes comprise four transmitting optical fiber probes and four receiving optical fiber probes; the eight mounting holes are respectively used for mounting the four transmitting optical fiber probes and the four receiving optical fiber probes;
   the two mounting holes on each boss are respectively used for mounting one transmitting optical fiber probe of the four transmitting optical fiber probes and one receiving optical fiber probe of the four receiving optical fiber probes; and the two mounting holes at the upper side and the lower side of the outer ring of the coil are respectively used for mounting one transmitting optical fiber probe of the four transmitting optical fiber probes and one receiving optical fiber probe of the four receiving optical fiber probes.

2. The integrated TMS coil for brain function testing and treatment according to claim 1, wherein,
   the coil is formed by winding a hollow copper tube, and an interior of the hollow copper tube is used for circulating a cooling liquid;
   a water inlet and a water outlet are formed at a position where the coil is connected to the TMS instrument, and the water inlet and the water outlet are respectively in communication with two ports of the hollow copper tube;
   a TMS host, a water pump, a water tank, and a radiator are provided inside the TMS instrument; the water pump is separately in communication with the water tank and the water inlet, and the radiator is separately in communication with the water outlet and the water tank; and
   the cooling liquid is circulated in the water tank, the hollow copper tube, and the radiator to cool the coil.

3. The integrated TMS coil for brain function testing and treatment according to claim 1, wherein,
   each optical fiber holder comprises an annular boss and a nut, and the nut is threadedly connected to the annular boss; an inner diameter of the annular boss is slightly less than an outer diameter of the respective optical fiber probe to facilitate sleeving of an optical fiber; and
   an outer diameter of an upper part of the annular boss is greater than a caliber of a respective through hole on the silica gel sheet, and the respective through hole on the silica gel sheet is sleeved on the upper part of the annular boss.

4. The integrated TMS coil for brain function testing and treatment according to claim 1, wherein,
   a buffer silica gel head is provided on an end of each optical fiber probe adapted to be contact with a scalp of a patient.

5. The integrated TMS coil for brain function testing and treatment according to claim 1, wherein,
   each optical fiber holder is made of plastic.

6. The integrated TMS coil for brain function testing and treatment according to claim 5, wherein,
   the coil housing is made of an insulating and thermal insulating material.

7. The integrated TMS coil for brain function testing and treatment according to claim 1, wherein,
   a plurality of cable tie holes are formed on a side surface of the coil housing.

8. The integrated TMS coil for brain function testing and treatment according to claim 1, wherein,
   a front of the coil housing is a concave are surface, and a radius of the concave are surface is 100 mm.

* * * * *